(12) United States Patent
Nakasugi et al.

(10) Patent No.: US 8,030,227 B2
(45) Date of Patent: Oct. 4, 2011

(54) PHOTOCURABLE FIXTURE FOR ORTHOPEDIC SURGERY

(75) Inventors: Nobuyasu Nakasugi, Kyoto (JP); Yoshikazu Matsumoto, Funabashi (JP)

(73) Assignee: Alcare Co., Ltd. (JP)

( * ) Notice: Subject to any disclaimer, the term of this patent is extended or adjusted under 35 U.S.C. 154(b) by 79 days.

(21) Appl. No.: 11/795,674

(22) PCT Filed: Feb. 13, 2006

(86) PCT No.: PCT/JP2006/002477
§ 371 (c)(1),
(2), (4) Date: Jul. 19, 2007

(87) PCT Pub. No.: WO2006/090605
PCT Pub. Date: Aug. 31, 2006

(65) Prior Publication Data
US 2008/0045622 A1   Feb. 21, 2008

(30) Foreign Application Priority Data
Feb. 24, 2005   (JP) .................................. 2005-048203

(51) Int. Cl.
A61L 15/07   (2006.01)
A61F 12/04   (2006.01)
B32B 27/04   (2006.01)

(52) U.S. Cl. ........ 442/104; 442/152; 442/153; 442/164; 442/179; 442/180; 522/64; 522/66; 522/173; 602/2; 602/76

(58) Field of Classification Search .................. 522/173, 522/64, 66, 74, 8, 71; 442/105, 164, 180, 442/152, 153, 179; 602/2, 76
See application file for complete search history.

(56) References Cited

U.S. PATENT DOCUMENTS
4,052,282 A * 10/1977 Kubushiro .................... 602/8
(Continued)

FOREIGN PATENT DOCUMENTS
JP   01242612   9/1989
(Continued)

*Primary Examiner* — Susan W Berman
(74) *Attorney, Agent, or Firm* — Adams & Wilks

(57) ABSTRACT

A photocurable fixture for orthopedic surgery has a base material and a photocurable resin retained in the base material and containing a urethane (meth)acrylate oligomer and a photopolymerization initiator which absorbs a light within a range of 400 to 700 nm. The urethane (meth)acrylate oligomer being represented by the following formula (I), $$X-O-\underset{\underset{O}{\|}}{C}-\underset{H}{N}-A-\underset{H}{N}-\underset{\underset{O}{\|}}{C}-O-Y \qquad (I)$$

where A denotes a diisocyanate residue, and each of X and Y denotes a residue obtained by removing a hydroxy group from a (meth)acrylate having a hydroxy group. In formula (I) at least 40 mol % of X and Y is a residue obtained by removing a hydroxy group from a (meth)acrylate having a hydroxy group represented by the following formula (II), $$R_1-\underset{\underset{O}{\|}}{\overset{CH_2}{\overset{\|}{C}}}-\overset{}{C}-O-CH_2-\underset{\underset{}{\overset{OH}{|}}}{CH}-CH_2-O-\underset{R_6\ R_5}{\overset{R_2\ R_3}{\bigcirc}}-R_4 \qquad (II)$$

where in Formula (II) each of R1 to R6 denotes a hydrogen atom or a methyl group.

8 Claims, 2 Drawing Sheets

U.S. PATENT DOCUMENTS

| | | | |
|---|---|---|---|
| 4,316,457 A * | 2/1982 | Liegeois | 602/42 |
| 4,512,340 A * | 4/1985 | Buck | 602/2 |
| 4,655,202 A * | 4/1987 | Potter et al. | 602/8 |
| 4,985,472 A * | 1/1991 | Aosai et al. | 522/64 |
| 5,913,840 A * | 6/1999 | Allenberg et al. | 602/8 |
| 6,635,691 B2 * | 10/2003 | Zanghellini et al. | 523/105 |
| 7,108,952 B2 * | 9/2006 | Sugasaki et al. | 430/270.1 |

FOREIGN PATENT DOCUMENTS

| | | |
|---|---|---|
| JP | 2001316416 | 11/2001 |
| JP | 2002012635 | 1/2002 |
| JP | 2002291861 | 10/2002 |
| WO | 2004044040 | 5/2004 |

* cited by examiner

PHOTOCURABLE FIXTURE FOR ORTHOPEDIC SURGERY

CROSS-REFERENCE TO RELATED APPLICATIONS

This application is a U.S. national stage application of International Application No. PCT/JP2006/302447, filed Feb. 13, 2006, claiming a priority date of Feb. 24, 2005, and published in a non-English language.

FIELD OF THE INVENTION

The present invention relates to a fixture for orthopedic surgery, for forming a splint, cast, stay, etc. which fixes or supports affected or diseased parts for treatment or protection in the fields of medical care or sports. More particularly, it relates to a fixture for orthopedic surgery, for treatment or prevention of fracture, sprain, correction, etc. of human being or animals, and for protection of bodies from stumble, shock, etc. in sports, etc.

BACKGROUND INFORMATION

As surgical bandage used for treatment of fracture or fixture of other parts of body, ones having plaster of Paris retained in a fiber base material such as gauze have been employed from the old times. However, the surgical bandage has drawbacks such that it is heavy, insufficient in strength, and less water resistant, and does not allow X-rays pass through it.

As a method for solving such problems, ones having a water-curable urethane prepolymer impregnated into a base material of fabric or knit of e.g. glass fibers have been employed as a bandage for orthopedic surgery. Further, one having such a water-curable resin retained in a base material is wrapped with a covering material, and used as a splint material.

The fixture for orthopedic surgery using such water-curable resins is highly water resistant and has a high strength. Further, since it is possible to have X-ray photography with this fixture attached, this fixture has been widely used.

However, with this fixture, it is required to make the water-curable resin in fully contact with water by dipping the whole fixture in water stored in a bucket or the like, in order to facilitate curing reaction smoothly. Accordingly, it cannot be used in the lack of water, such being inconvenient. Further, since a backing of a cast material or a cover at the skin side of the splint material is soaked with water, the affected parts to which the fixture is applied get wet and the unpleasant feeling may sometimes be given. Further, when the affected parts are required to be fixed immediately after surgery, it may sometimes be impossible to use this fixture in a germ-free condition.

On the other hand, it has been proposed from the old days to impregnate a photocurable resin into woven fabric of e.g. glass fibers and cure it with light. As such photocurable resin, it was at first proposed to use an ultraviolet curable resin (Document 1). It was then proposed to use a visible light curable resin (Document 2).

Document 1: JP-B-48-6116
Document 2: JP-A-4-8367

Despite such various proposals, fixtures for orthopedic surgery using photocurable resins have not been used in practice for the following reasons. These photocurable resin compositions require an intense light or irradiation for a long time and a large-sized irradiation machine may sometimes be demanded. Further, a photosensitizer may sometimes be required in a relatively large amount. Furthermore, some components of such resin compositions have a strong odor or are highly skin stimulative such being inappropriate for this purpose. Moreover, there are problems of insufficient storage stability and insufficient strength.

As problems of radical polymerization in photo-curing, there are inconveniences such that polymerization is inhibited by oxygen in air and unreacted components remain on the surface of the cured product to give tackiness.

The visible light-curable fixtures for orthopedic surgery heretofore employed, use a urethane (meth)acrylate. This urethane (meth)acrylate is obtained by adding a (meth)acrylate having a hydroxy group to a urethane prepolymer derived from a polyol and isocyanate.

Further, as the photopolymerization initiator used for the photocurable resin of a visible light-curable type, one containing camphorquinone has been used.

The fixture for orthopedic surgery is required to exhibit a high strength and a high hardness of the cured product since it fixes the affected parts. For this purpose, it is required to cure ones laminated in a multi-layer form and further conduct the curing in air. Further, the photocurable resin is required to have a composition that shows desired performance even if polymerization is inhibited by oxygen in air.

SUMMARY OF THE INVENTION

Under such circumstances, the present invention provides a photocurable fixture for orthopedic surgery which has no such drawbacks, exhibits the desired strength in a short period of time by only irradiation with visible light, generates no unpleasant odor, can easily be used and can be readily produced.

The present inventors have conducted extensive studies to solve the above-mentioned problems and as the result, found that the above desired photocurable fixture for orthopedic surgery can be obtained by comprising a base material, and a photocurable resin containing a urethane (meth)acrylate oligomer represented by the following formula (I) and a photopolymerization initiator which absorbs a light within a range of 400 to 700 nm, retained in the base material. In the following formula (I), A denotes a diisocyanate residue, and each of X and Y denotes a (meth)acrylate residue having a hydroxy group.

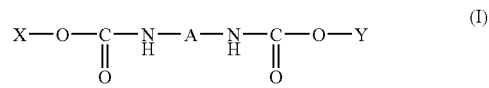

As the compound of the formula (I), it is preferred to use a compound of the formula (I) wherein at least 40 mol % of X and Y is a residue represented by the following formula (II) obtained by removing a hydroxy group from a (meth)acrylate having a hydroxy group,

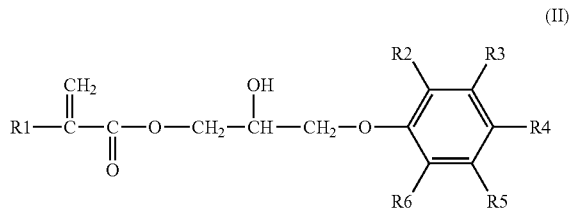

(in the formula (II), each of R1 to R6 denotes a hydrogen atom or a methyl group).

Further, by using a bisacylphosphine oxide type photopolymerization initiator represented by the following formula (III) as the photopolymerization initiator, an excellent photocurable fixture for orthopedic surgery can be obtained.

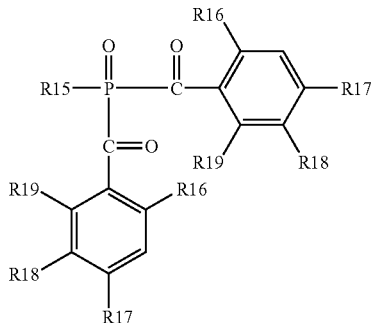

(in the formula (III), R15 denotes a straight chain or branched chain $C_{1-12}$ alkyl group, a cycloalkyl group, an aryl group which may be substituted by a straight chain or branched chain $C_{1-12}$ alkyl group or a halogen atom; each of R16 and R17 which may be the same or different, denotes a hydrogen atom, a straight chain or branched chain $C_{1-12}$ alkyl group, or a straight chain or branched chain $C_{1-12}$ alkoxy group; and each of R18 and R19 which may be the same or different, denotes a hydrogen atom, or a straight chain or branched chain $C_{1-12}$ alkyl group).

Further, by using a bis(2,4,6-trimethylbenzoyl)phenyl phosphine oxide as the photopolymerization initiator of the formula (III), a further preferred photocurable fixture for orthopedic surgery can be obtained.

Moreover, as the photopolymerization initiator, a titanocene type photopolymerization initiator represented by the following formula (IV) may be used.

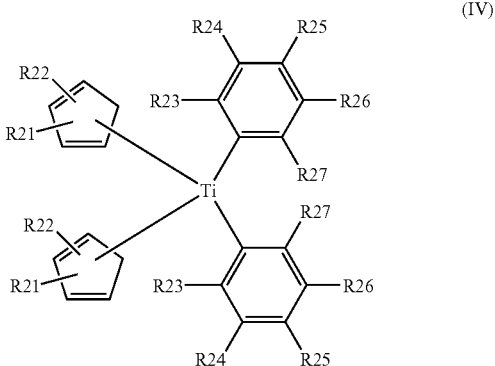

(in the formula (IV), each of R21 and R22 independently denotes a hydrogen atom or a methyl group; R23 denotes a fluorine atom, —$CF_3$ or —$CF_2CH_3$; and each of R24, R25, R26 and R27 independently denotes a hydrogen atom, a fluorine atom, —$CF_3$, —$CF_2CH_3$, a $C_1$-$C_{12}$ alkyl group or alkoxy group, a 6-membered carbocyclic aromatic group, or a 5- or 6-membered heterocyclic aromatic group).

Further, by using bis(cyclopentadienyl)-bis(2,6-difluoro-3-(pyrrol-1-yl)phenyl)titanium as the photopolymerization initiator of the formula (IV), a preferred photocurable fixture for orthopedic surgery can be obtained.

As mentioned above, in the present invention, it is possible to obtain a photocurable fixture for orthopedic surgery which shows necessary strength in a short period of time by applying visible light. Further, under the light at the level of general lighting from the ceiling in room, this fixture allows a working period of at least 20 minutes (time within which the fixture for orthopedic surgery can be applied in a formable fashion to affected parts). Accordingly, when this fixture is applied to affected parts, sufficient working period can be obtained to fix it appropriately.

Further, since water is not used for curing, no stain due to water is seen in surgical operation. Furthermore, this fixture can be used effectively with visible light even in treatment of fracture, etc. at the site in which water cannot be readily prepared, for example, disaster area or desert. Particularly, in a case where the fixing function in a sterile condition is required after operation, this fixture is very effective since contamination due to the use of water can be prevented.

DETAILED DESCRIPTION OF THE PREFERRED EMBODIMENTS

Figure 1:
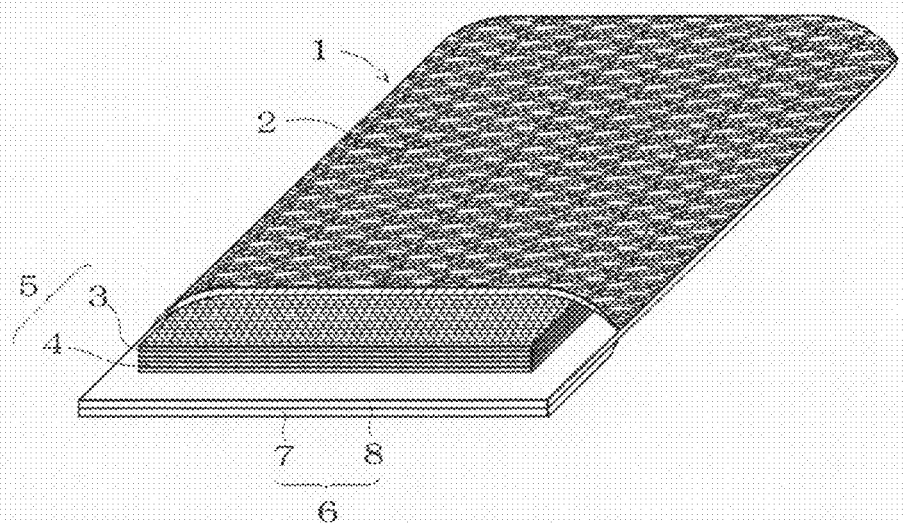
FIG. 1 is a partially cutaway perspective view showing an example of the present invention.
Figure 2:
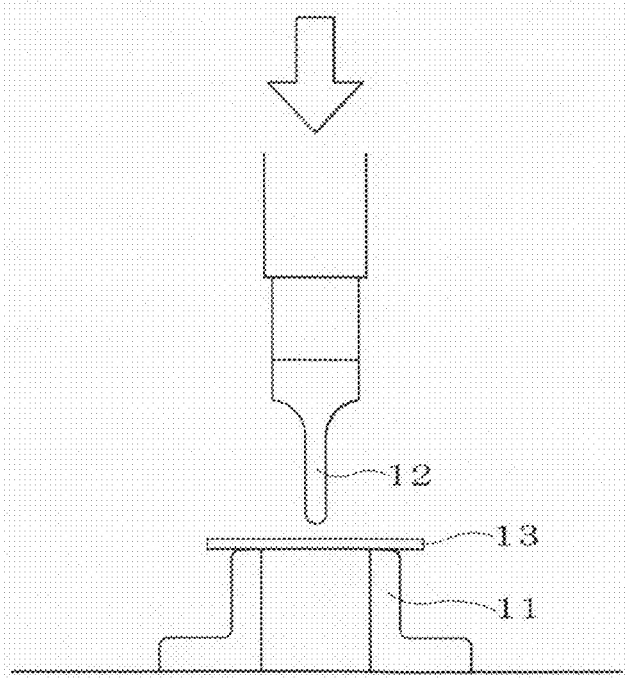
FIG. 2 is an explanatory view of a bending strength test of the present invention.
Figure 3:
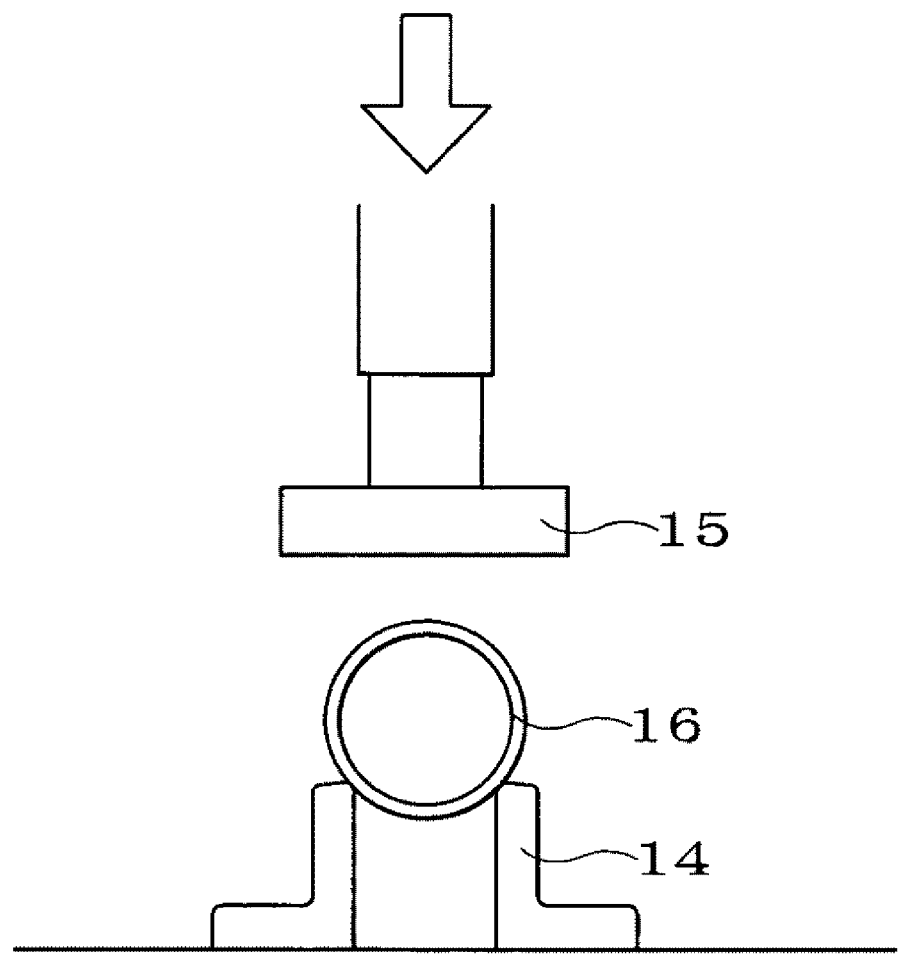
FIG. 3 is an explanatory view of a cylinder strength test of the present invention.

Hereinafter, the present invention will be explained in detail.

The urethane (meth)acrylate oligomer represented by the formula (I) is obtained by a reaction of diisocyanate with a (meth)acrylate having a hydroxy group.

The diisocyanate used in the present invention may, for example, be an aromatic diisocyanate such as 2,4-tolylene diisocyanate, 2,6-tolylene diisocyanate, 4,4'-diphenylmethane diisocyanate, 2,4'-diphenylmethane diisocyanate or p-phenylene diisocyanate; an aliphatic polyisocyanate such as hexamethylene diisocyanate; an alicyclic polyisocyanate such as 3-isocyanatomethyl-3,5,5-trimethylcyclohexyl isocyanate or 4,4'-dicyclohexylmethane diisocyanate; and an aryl aliphatic polyisocyanate such as xylylene diisocyanate. These may be used singly or in combination of at least two.

Preferred isocyanates are an aliphatic isocyanate and an alicyclic polyisocyanate, and particularly preferred is hexamethylene diisocyanate.

The (meth)acrylate having a hydroxy group used in the present invention may, for example, be a hydroxyalkyl (meth)acrylate such as 2-hydroxyethyl(meth)acrylate, 2-hydroxypropyl(meth)acrylate, 3-hydroxypropyl (meth)acrylate, pentanediol mono(meth)acrylate, hexanediol mono(meth)acrylate or neopentyl glycol mono(meth)acrylate; 2-hydroxyalkyl(meth)acryloyl phosphate, 4-hydroxycyclohexyl (meth)acrylate, trimethylolpropanedi(meth)acrylate, pentaerythritoltri(meth)acrylate and 3-methacryloyloxy-2-hydroxypropyl(meth)acrylate.

Further, a compound produced by an addition reaction of a glycidyl group- or epoxy group-containing compound with a (meth)acrylic acid may, for example, be mentioned. The glycidyl group- or epoxy group-containing compound may, for example, be phenyl glycidyl ether, 2-methylphenyl glycidyl ether, 3-methylphenyl glycidyl ether, 4-methylphenyl glycidyl ether, 2,4-dimethylphenyl glycidyl ether, 2,6-dimethyl glycidyl ether, 2,4,6-trimethyl glycidyl ether, butyl glycidyl ether and glycidyl(meth)acrylate.

These (meth)acrylates having a hydroxy group may be used singly or in combination of at least two.

Preferred (meth)acrylate having a hydroxy group is a compound produced by an addition reaction of a glycidyl group- or epoxy group-containing compound with a (meth)acrylic acid, and particularly preferred one is a (meth)acrylic acid addition reaction product of phenyl glycidyl ether.

The urethane (meth)acrylate oligomer may be obtained by reacting 0.8 to 1.2 mol of diisocyanate with 2 mol of a (meth) acrylate having a hydroxy group.

Reaction methods of these components are not particularly limited, but in general, respective components are mixed at once and reacted at 20 to 120° C.

In such urethane formation reaction, well known metal catalysts and amine type catalysts may be used.

Preferred urethane (meth)acrylate oligomer is one containing a (meth)acrylate having a hydroxy group of the formula (II) in an amount of at least 40 mol % of the total (meth) acrylates having a hydroxy group.

In the photocurable resin of the present invention, a urethane (meth)acrylate oligomer other than the above-mentioned ones (hereinafter referred to as urethane (meth)acrylate oligomer (B)), and an ethylenic unsaturated compound may be used in combination. The urethane (meth)acrylate oligomer (B) may be obtained by a urethane formation reaction of polyisocyanate, polyol and a (meth)acrylate having a hydroxy group.

As the polyisocyanate used for the urethane formation reaction, in addition to the above diisocyates, carbodiimide-modified or isocyanurate-modified polyisocyanate thereof may be mentioned. These may be used singly or in combination of at least two.

As the polyol, a low molecular weight polyol such as ethylene glycol, propylene glycol or glycerol may be mentioned. Further, a polyether polyol obtained by adding an alkylene oxide such as ethylene oxide or propylene oxide, to a polyphenol such as hydroquinone or bisphenol A; an amine such as aniline, ethylenediamine or diethylenetriamine; or a low molecular weight polyol, may be mentioned. Furthermore, a polyester polyol obtained by a dehydration condensation reaction of a low molecular weight polyol with a dicarboxylic acid such as adipic acid or phthalic acid, may be mentioned. Moreover, a polylactone polyol obtained by a ring-opening polymerization of lactone products such as γ-butyrolactone or ε-caprolactone; and polytetramethylene glycol obtained by a ring-opening polymerization of tetrahydrofuran, may be mentioned. Castor oil or its alkylene oxide adduct; a polydiene polyol which is a polymerized product of a diene compound such as butadiene or isoprene and which has a hydroxy group at the terminal, or its hydrogenated product, may also be mentioned. These may be used singly or in combination of at least two.

As the (meth)acrylate having a hydroxy group, the above-mentioned (meth)acrylate having a hydroxy group may be mentioned.

The urethane (meth)acrylate oligomer (B) may be prepared by reacting the above components. As the proportion of the respective components constituting the urethane (meth)acrylate oligomer (B), for example, 0.4 to 0.8 equivalent amount of the hydroxy group (OH group) of the polyol component and about 0.2 to 0.6 equivalent amount of the (meth)acrylate having a hydroxy group are used to 1 equivalent amount of the isocyanate group (NCO group) of polyisocyanate.

Further, the reaction process of the above components is not particularly limited. In general, it is preferred that polyisocyanate and a polyol component are reacted first and then reacted with a (meth)acrylate having a hydroxy group.

In the urethane formation reaction of the above components, well known urethane formation catalysts (a metal type catalyst or an amine type catalyst) may be used.

The ethylenic unsaturated compound may include a monofunctional compound, a difunctional compound and a multifunctional compound.

The monofunctional compound may, for example, be N-vinyl pyrrolidone, acryloyl morpholine, N-vinyl acetamide, N-vinyl formamide, N,N'-dimethyl acrylamide, dimethyl aminoethyl (meth)acrylate, diethyl aminoethyl(meth)acrylate, or an alkoxypolyalkylene glycol (meth)acrylate such as methoxyethylene glycol (meth)acrylate, methoxypolyethylene glycol (meth)acrylate or butoxypolyethylene glycol (meth)acrylate. Further, nonylphenoxyethyl(meth)acrylate, phenoxyethyl(meth)acrylate, phenoxy polyethylene glycol (meth)acrylate, cumylphenolpolyalkylene (meth)acrylate, cyclohexyl(meth)acrylate, benzyl(meth)acrylate, dicyclopentenyl(meth)acrylate, and tricyclodecanyl (meth)acrylate may be mentioned.

The difunctional compound may, for example, be ethylene glycol di(meth)acrylate, polyethylene glycol di(meth)acrylate, propylene glycol di(meth)acrylate, polypropylene glycol di(meth)acrylate, 1,4-butanediol di(meth)acrylate, 1,6-hexanediol di(meth)acrylate, neopentyl glycol di(meth) acrylate, pentanediol di(meth)acrylate, or di(meth)acrylate of an alkylene oxide (ethylene oxide, propylene oxide, butylene oxide or the like) adduct of bisphenol A.

Further, the multifunctional compound may, for example, be trimethylolpropane tri(meth)acrylate, trimethylolpropane trioxyethyl(meth)acrylate, pentaerythritol tri(meth)acrylate, dipentaerythritol hexa(meth)acrylate, tris(acryloyloxy)isocyanurate, tri(meth)acrylate of tris(2-hydroxyethyl)isocyanurate, tri(meth)acrylate of tris(hydroxypropyl)isocyanurate, triaryltrimellitic acid or triarylisocyanurate.

These ethylenic unsaturated compounds may be used singly or in combination of at least two. When the ethylenic unsaturated compound is used, selection should be made taking due care about odor or skin stimulative property.

The amounts of the urethane (meth)acrylate oligomer (B) and ethylenic unsaturated compound are selected depending on the type of the urethane (meth)acrylate oligomer and ethylenic unsaturated compound, the desired viscosity of the resin composition, etc. For example, the amount may be selected from a range of at most 50 parts by weight, preferably at most 20 parts by weight, more preferably at most 5 parts by weight, to 100 parts by weight of the urethane (meth)acrylate oligomer of the formula (I).

In the present invention, a photopolymerization initiator which absorbs a light within a range of 400 to 700 nm is used. As such a compound, a bisacylphosphine oxide type photopolymerization initiator represented by the following formula (III) may be used.

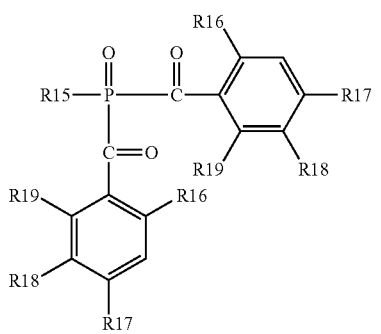

(III)

(in the formula (III), R15 denotes a straight chain or branched chain $C_{1-12}$ alkyl group, a cycloalkyl group, an aryl group which may be substituted by a straight chain or branched chain $C_{1-12}$ alkyl group or a halogen atom; each of R16 and R17 which may be the same or different, denotes a hydrogen atom, a straight chain or branched chain $C_{1-12}$ alkyl group, or a straight chain or branched chain $C_{1-12}$ alkoxy group; and each of R18 and R19 which may be the same or different, denotes a hydrogen atom, or a straight chain or branched chain $C_{1-12}$ alkyl group.)

As the straight chain or branched chain $C_{1-12}$ alkyl group in the above formula (III), methyl, ethyl, propyl, isopropyl, butyl, s-butyl, t-butyl, pentyl, isopentyl, 2,4,4-trimethylpentyl, hexyl, isohexyl, 2,4,4-trimethylhexyl, octyl, decyl and dodecyl groups may, for example, be mentioned.

As R15, preferred one is a branched chain $C_{6-12}$ alkyl group, and particularly preferred is a branched chain $C_{6-10}$ alkyl group.

As the cycloalkyl group, a $C_{3-10}$ cycloalkyl group such as a cyclopentyl, cyclohexyl or cyclooctyl group may be mentioned, and a $C_5$-10 cycloalkyl group may preferably be mentioned.

The aryl group may include phenyl and naphthyl groups, and the aryl group may be substituted by a straight chain or branched chain $C_{1-12}$ alkyl group or a halogen atom. The $C_{1-12}$ alkyl group includes alkyl groups as previously mentioned, and is generally preferably a straight chain or branched chain $C_{1-4}$ alkyl group (methyl, ethyl, propyl, isopropyl, butyl, t-butyl or the like).

The halogen atom includes fluorine, chlorine, bromine and iodine atoms.

Further, the straight chain or branched chain $C_{1-12}$ alkoxy group may, for example, be methoxy, ethoxy, propoxy, isopropoxy, butoxy, isobutoxy, s-butoxy, t-butoxy, pentyloxy, hexyloxy or octyloxy group. Preferred alkoxy group is a straight chain or branched chain $C_{1-4}$ alkoxy group. Further, preferred combination of R15 to R19 is as follows:

R15: a $C_{1-12}$ alkyl group (particularly a branched chain $C_{6-12}$ alkyl group), or an aryl group (particularly a phenyl group), R16 and R17: a $C_{1-4}$ alkyl group (particularly a $C_{1-2}$ alkyl group) or a $C_{1-4}$ alkoxy group (particularly a $C_{1-2}$ alkoxy group), and R18 and R19: a hydrogen atom or a $C_{1-4}$ alkyl group (particularly a methyl group).

The bisacylphosphine oxide type photopolymerization initiator may include a bis(2,6-di $C_{1-2}$ alkoxybenzoyl)-branched chain $C_{6-12}$ alkylphosphine oxide such as bis(2,6-dimethoxybenzoyl)-2,4,4-trimethyl pentyl phosphine oxide. Further, a bis(2,4,6-tri $C_{1-2}$ alkylbenzoyl) $C_{1-6}$ alkylphosphine oxide such as bis(2,4,6-trimethylbenzoyl)methylphosphine oxide, bis(2,4,6-trimethylbenzoyl)ethylphosphine oxide or bis(2,4,6-trimethylbenzoyl)-n-butylphosphine oxide, may also be included. Moreover, bis(2,4,6-tri $C_{1-2}$ alkylbenzoyl) arylphosphine oxide such as bis(2,4,6-trimethylbenzoyl)phenylphosphine oxide may be mentioned. These bisacylphosphine oxide type photopolymerization initiators may be used singly or in combination of at least two. Preferred is bis(2,4,6-trimethylbenzoyl)phenylphosphine oxide.

Further, as the photopolymerization initiator which absorbs a light within a range of 400 to 700 nm, a titanocene type photopolymerization initiator represented by the following formula (IV), camphorquinone, etc. may be used.

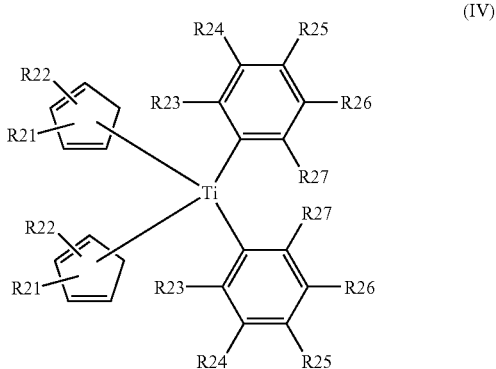

(IV)

(in the formula (IV), each of R21 and R22 independently denotes a hydrogen atom or a methyl group; R23 denotes a fluorine atom, $-CF_3$ or $-CF_2CH_3$; and each of R24, R25, R26 and R27 independently denotes a hydrogen atom, a fluorine atom, $-CF_3$, $-CF_2CH_3$, a $C_1$-$C_{12}$ alkyl group or alkoxy group, a 6-membered carbocyclic aromatic group, or a 5- or 6-membered heterocyclic aromatic group).

The titanocene type photopolymerization initiator may, for example, be bis(cyclopentadienyl)-diphenyltitanium, bis(cyclopentadienyl)-bis(2,3,4,5,6-pentafluorophenyl)titanium, bis(cyclopentadienyl)-bis(2,3,5,6-tetrafluorophenyl)titanium, bis(cyclopentadienyl)-bis(2,4,6-trifluorophenyl)titanium, bis(cyclopentadienyl)-bis(2,6-difluorophenyl)titanium, bis(cyclopentadienyl)-bis(2,4-difluorophenyl)titanium, bis(methylcyclopentadienyl)-bis(2,3,4,5,6-pentafluorophenyl)titanium, bis(methylcyclopentadienyl)-bis(2,3,5,6-tetrafluorophenyl)titanium, bis(methylcyclopentadienyl)-bis(2,6-difluorophenyl)titanium, bis(cyclopentadienyl)-bis(2,6-difluoro-3-(pyrrol-1-yl)phenyl)titanium, bis(cyclopentadienyl)-bis(2,4,6-trifluoro-3-(pyrrol-1-yl)phenyl)titanium, and bis(cyclopentadienyl)-bis(2,4,6-trifluoro-3-(2,5-dimethylpyrrol-1-yl)phenyl)titanium. These titanocene type photopolymerization initiators may be used singly or in combination of at least two. Preferred titanocene type photopolymerization initiator is bis(cyclopentadienyl)-bis(2,6-difluoro-3-(pyrrol-1-yl)phenyl)titanium.

The above-mentioned bisacylphosphine oxide type photopolymerization initiator, titanocene type photopolymerization initiator and camphorquinone may be used in combination appropriately with other photopolymerization initiator (for example, an acetophenone type or propiophenone type photopolymerization initiator, a benzyl type, benzoin type or benzophenone type photopolymerization initiator, or a thioxanthone type photopolymerization initiator).

The acetophenone type or propiophenone type photopolymerization initiator may, for example, be an acetophenone such as 2,2-dimethoxy-2-phenyl acetophenone, acetophenone diethylketal or diethoxy acetophenone, or its derivative;

or an oligomer of 2-hydroxy-2-methyl-1-phenylpropan-1-one, 2-benzyl-2-dimethylamino-1-(4-morpholinophenyl)-butanone, 2-methyl-2-morpholino(4-thiomethylphenyl)propan-1-one or 2-hydroxy-2-methyl-1-[4-(1-methylvinyl)phenyl]propanone.

As the benzyl type photopolymerization initiator, benzyl and benzyl dimethylketal may be mentioned.

Further, as the benzoin type photopolymerization initiator, benzoin, benzoin methyl ether, benzoin ethyl ether, benzoin isopropyl ether, benzoin isobutyl ether or the like may be mentioned.

The benzophenone type photopolymerization initiator may, for example, be benzophenone, methyl o-benzoyl benzoate, 4-phenyl benzophenone, 3,3'-dimethyl-4-methoxy benzophenone, 4,4'-methoxy benzophenone, 4-benzoyl-4'-methyldiphenyl sulfide, 2,4,6-trimethyl benzophenone and (4-benzoylbenzyl)trimethylammonium chloride.

Further, the thioxanthone type photopolymerization initiator may, for example, be 2- or 4-isopropyl thioxanthone, 2,4-diethyl thioxanthone and 2,4-dichloro thioxanthone.

Furthermore, other photopolymerization initiator may, for example, be 1-hydroxycyclohexyl phenyl ketone, methylphenyl glyoxy ester and 3,6-bis(2-morpholino isobutyl)-9-butyl carbazole.

The amount of the photopolymerization initiator is about 0.01 to 10 parts by weight, preferably 0.05 to 2 parts by weight, to 100 parts by weight of the urethane (meth)acrylate oligomer or 100 parts by weight of the total amount of the urethane (meth)acrylate oligomer, urethane (meth)acrylate oligomer (B) and ethylenic unsaturated compound.

In the photocurable resin of the present invention, a photosensitizer may further be incorporated as the case desires.

Such photosensitizer may be a coumarin derivative such as 7-diethylamino-3-(2-benzothiazolyl)coumarin, 7-diethylamino-3-(2-benzimidazolyl)coumarin, 7-diethylamino-3-benzoylcoumarin, 7-diethylamino-3-thiazolylcoumarin, 7-diethylamino-3,3'-carbonylbiscoumarin, 7-diethylamino-3-(4-tert-butyldioxy carbonyl methoxybenzoyl)coumarin or 5,7-dimethoxy-3-(4-tert-butyldioxy carbonyl methoxybenzolyl)coumarin. Further, a xanthene dye such as eosine, ethyl eosine, erythrosine, fluorescein, rose Bengal; a triarylmethane dye; a methine dye; an azo dye; a cyanine dye; a thiopyrylium dye; a diphenyliodonium dye; and a pyromethene complex such as 2,6-diethyl-1,3,5,7,8-pentamethyl pyromethene-$BF_2$ complex or 1,3,5,7,8-pentamethyl pyromethene-$BF_2$ complex, may be mentioned. Furthermore, a ketothiazoline compound such as 1-(1-methylnaphtho[1,2-d]thiazol-2(1H)-ylidene-4-(2,3,6,7) tetrahydro-1H, 5H-benzo[ij]quinolizin-9-yl)-3-buten-2-one, or 1-(3-methyl benzothiazol-2(3H)-ylidene-4-(p-dimethylamino phenyl)-3-buten-2-one; a styryl or phenylbutadienyl heterocyclic compound such as 2-(p-dimethylamino styryl)-naphtho[1,2-d]thiazole or 2-[4-(p-dimethyamino phenyl)-1,3-butadienyl]-naphtho[1,2-d]thiazole; and a triazine compound such as 2,4-diphenyl-6-(p-dimethylamino styryl)-1,3,5-triazine, 2,4-diphenyl-6-(([2,3,6,7]tetrahydro-1H,5H-benzo[ij]quinolizin-9-yl)-1-ethen-2-yl)-1,3,5-triazone, may be mentioned. Further, an aminophenyl unsaturated ketone compound such as 9-phenanthryl-(([2,3,6,7]tetrahydro-1H,5H-benzo[ij]quinolizin-9-yl)-1-ethen-2-yl)ketone or 2,5-bis(p-dimethylaminocinnamylidene)cyclopentanone; a porphyrin such as 5,10,15,20-tetraphenylporphyrin or hematoporphyrin may, for example, be mentioned.

Various types of photopolymerization promoters may be added to the photocurable resin composition of the present invention, if the case requires, in order to accelerate the photopolymerization reaction with a photopolymerization initiator. Such photopolymerization promoters may, for example, include a dialkylaminobenzoic acid or its derivative such as 4-dimethylaminobenzoic acid, 4-dimethylaminobenzoic acid ester, an arylphosphine such as triphenylphosphine, and a phosphine compound such as a trialkylphosphine. These photopolymerization promoters may be used singly or in combination of at least two.

As the amount of the photopolymerization promoter, it may be selected from the range of about 0.01 to 10 parts by weight to 100 parts by weight of the urethane (meth)acrylate oligomer or 100 parts by weight of the total amount of the urethane (meth)acrylate oligomer, urethane (meth)acrylate oligomer (B) and ethylenic unsaturated compound.

To the photocurable resin of the present invention, various types of additives may be added depending on the purpose or necessity of the fixture. Such additives may be a polymerization inhibitor (hydroquinone, methoxyhydroquinone or the like), an antioxidant, a tacky-free agent (silicone oil or the like), a thixotropy-imparting agent (castor oil fatty acid amide, dibenzylidene sorbitol or the like), a dye, a pigment, a silane coupling agent, a surfactant, a colorant, organic or inorganic fine particles, etc.

The base material of the present invention is used to retain the photocurable resin so as to form a fixture for orthopedic surgery. As such a base material, woven fabric, knit, non-woven fabric, etc. using various types of fibers may be used. As the fibers, natural fibers (cellulose fibers, protein fibers, etc.), and chemical fibers (regenerated fibers, semi-synthetic fibers, synthetic fibers, inorganic fibers, etc.), may be used. For example, cotton, wool, rayon, polyamide fibers, polyester fibers, acryl fibers, polyolefin fibers, glass fibers, carbon fibers and other fibers may be mentioned. In general, as the base material, ones having a high modulus of elasticity in tension, for example, about 800 MPa or higher is suitable.

As the base material, knit obtained by Raschel knitting using aggregate (yarn) of glass fibers or polyester fibers is particularly preferably used.

As the light source for curing the photocurable fixture for orthopedic surgery of the present invention, a light source showing a light of 400 to 700 nm as the absorption wavelength of the photopolymerization initiator may be used. As the light source, a light source of visible light such as a fluorescent lamp used in an ordinary home, a halogen lamp, a krypton lamp or LED may be used. Further, as the case requires, a light source showing a wavelength of 400 nm or lower such as a black lamp or a high-pressure mercury-vapor lamp may be used.

Hereinbelow, a splint material as one embodiment of the fixture for orthopedic surgery of the present invention will be explained with reference to FIG. 1. In a splint material 1, a cover material 2 is disposed as the outermost layer (opposite side to affected parts), and inside it, a support material 5 comprising a base material 3 and a photocurable resin 4 retained therein is disposed. Further, at the inner side of this support material 5 (the side of affected parts of the support material), a buffer material 6 is disposed. The support material 5 is wrapped with the cover material 2 and buffer material 6. If necessary, the entire parts of the buffer material 6 and support material 5 are wrapped with the cover material 2.

In this figure, the photocurable resin 4 of the support material 5 is not exposed from the cover material 2, and even if this fixture is handled with naked hands over the cover material 2, the person will not touch the photocurable resin 4 directly. Further, when a self-adhesive bandage is wound over the cover material 2 of this splint material to fix it to the affected parts, uncured resin will not adhere to the bandage.

As such a cover material 2, one being capable of transmitting light and ventilating air and having an appropriate elasticity may preferably be used. Further, preferably, this cover material 2 does not allow the photocurable resin 4 to penetrate and reach the surface, and is unreactive with the photocurable resin 4. For example, its open area ratio is about 10 to 60%, preferably about 30 to 50%, and its thickness is about 0.05 to 8 mm, preferably about 1 to 4 mm. As the cover material 2, knit, woven fabric, nonwoven fabric, sheet, etc. using synthetic fibers of a polyfluoroethylene type, a polyester type, a polyolefin type, a polyvinyl chloride type, etc.; semi-synthetic fibers of rayon, etc.; natural fibers such as cotton, etc., may be used.

The open area ratio is a proportion of area where a void occupies within a certain range, and can be mechanically determined by taking an enlarged picture of a base material and carrying out image recognition.

With the cover material 2, it is preferred to conduct an oil repellent treatment with a fluorine system treatment agent so as to prevent attachment and penetration of an uncured photocurable resin 4. The fluorine system treatment agent may, for example, include a copolymer comprising as the main component an acrylic acid derivative (perfluoro monomer) prepared by an esterification of a compound having a perfluoroalkyl group and a hydroxy group with acrylic acid, methacrylic acid or the like. As the copolymer component, a monomer such as an alkyl(meth)acrylate or vinyl chloride, a crosslinkable monomer such as 2-hydroxyethyl(meth)acrylate or N-methylacrylamide, may be used.

Further, if fibers of polyfluoroethylene type, etc. are used for the cover material 2, oil repellency may sometimes be obtained without the above special oil repellent treatment.

The buffer material 6 preferably has a buffering property such that the contact with affected parts is soft, and prevents transmittance of reaction heat of the photocurable resin 4 at the time of curing towards the affected parts. Further, preferably, it hardly allows an uncured photocurable resin 4 to penetrate to the affected parts, and has an appropriate air permeability. Moreover, as the buffer material 6, preferred is one being unreactive with the photocurable resin 4 of the support material 5, flexible, and deformable such that it follows the shape of the affected parts, and having a good moldability.

For example, a thick nonwoven fabric using synthetic fibers such as a polyester type, a polyolefin type or a polyvinyl chloride type, semi-synthetic fibers of rayon, or natural fibers such as cotton; or a three-dimensional knit or woven fabric, may be mentioned. Further, a homogeneous foam of a single or composite body of e.g. a urethane type, a polyolefin type, or an ethylene/vinyl acetate copolymer (EVA); a foam having a skin layer; a laminate of the above respective materials; a combined structure of an nonwoven fabric or a three-dimensional knit/woven fabric with a foam, etc., may be used.

The thickness of the buffer material 6 is desirably as thin as possible so far as it has the above function, usually about 1 to 17 mm, preferably about 2 to 15 mm. If it is thinner than 1 mm, the above function is hardly available, and if it exceeds 17 mm, its moldability tends to be poor.

The buffer material 6 may be made of a multi-layer. In this instance, the lower layer (affected parts' side) is desirably one being capable of making the contact with the affected parts softer, and having air permeability, less skin-irritant properties and antibacterial properties. If one having air permeability is used for the lower layer, a material having no or less air permeability may be used for the upper layer (non-affected parts' side). In the fixture shown in the figure, nonwoven fabric of polyester fibers is used for a lower layer 7 of the buffer layer 6 and a foam sheet of an ethylene/vinyl acetate copolymer is used for an upper layer 8 thereof.

Depending on its application, a splint material formed in a fixed shape or a roll shape may be stored in a non-light-transmissive packaging material. With a large sized one of e.g. a roll shape, a desired amount is taken out from the packaging material and cut off, and the rest is returned to the packaging material, and it can be used in the same manner in the next time, whereby long time storage is possible.

When this splint material 1 is used, a splint material 1 is taken out from the non-light-transmissive packaging material, etc., and a buffer material side 6 of this splint material 1 is put directly on the affected parts, and its shape is given with hands from the outside. And, it is fixed by wrapping it with a bandage, etc. and molding is conducted by irradiation with visible light. Irradiation of visible light initiates the curing reaction of the photocurable resin 4 of the support material 5. As the curing proceeds gradually, the entire part is cured and the splint is finished. This splint can fix the affected parts and can be detached optionally if required.

A cast material as another embodiment of the fixture for orthopedic surgery of the present invention will be explained hereinbelow. In preparation of the cast material, a photocurable resin is applied on a base material made of the above-mentioned formed in a belt shape, and it is wound in a roll shape, and stored in a non-light-transmissive packaging material.

In use, it is taken out from the non-light-transmissive packaging material with hands wearing protective gloves such as rubber gloves. A protective material for skin is wound beforehand around the affected parts, and while rewinding the photocurable fixture of the roll shape, it is wound on the affected parts, and then it is cured by irradiation with light.

After the fixture is wound on the affected parts, before curing, if the photocurable fixture is covered with a thin nonwoven fabric, etc., it becomes possible to form the fixture by naked hands so that it fits to the affected parts. Further, since this nonwoven fabric covers the surface of the fixture even after the curing, it is possible to obtain a cast of a soft touch texture. Moreover, a separator may be disposed between a base material and another base material so that the woven fabric can be wound smoothly.

As further embodiment of the fixture for orthopedic surgery of the present invention, the fixture may be used as a stay material for various types of braces to be attached to the body. Namely, the fixture of the present invention may be used as a fixing material, a supporting material, a protecting material, etc. to impart strength to various types of braces such as an ankle brace, a knee joint brace, a low-back pain belt, or an upper limb orthosis. For example, in the above braces, a stay material is disposed for fixing, supporting or protecting, inside a flexible main body.

Such braces can likewise be kept in a non-light-transmissive packaging material. In use, the brace is taken out from the packaging material and applied to the site for use, and irradiation with light is conducted from the outside to cure the supporting material.

Further, the stay material may be covered with a cover material and stored in a non-light-transmissive packaging material. When this stay material is used, it is taken out from a packaging material and irradiated with light for curing, and then inserted into e.g. a pocket formed in the brace. The brace combined with the stay material this way is applied by putting it to the affected parts.

In this instance, the above stay material may be put in and taken out from the brace. Depending on the symptom, demands, etc. of patients, a stay material having an appropriate size, strength, etc. is combined with a brace, to further facilitate the preparation of a brace suitable for the symptom.

EXAMPLES

The following ones were prepared as the material and equipment.

(1) Urethane (Meth)Acrylate Oligomer

TABLE 1

| Trade name | Manufacturer | Composition |
| --- | --- | --- |
| AH-600 | Kyoeisha Chemical Co., Ltd | Urethane acrylate oligomer from phenyl glycidyl ether acrylate and hexamethylene diisocyanate |
| UA-306H | Kyoeisha Chemical Co., Ltd | Urethane acrylate oligomer from pentaerythritol acrylate and hexamethylene diisocyanate |
| Teslac 2324 | Hitachi Kasei Polymer Co., Inc. | Urethane acrylate oligomer from phenyl glycidyl ether acrylate/2-hydroxyethyl methacrylate (3/1 mixture) and hexamethylene diisocyanate |
| Teslac 2325 | Hitachi Kasei Polymer Co., Inc. | Urethane acrylate oligomer from phenyl glycidyl ether acrylate/2-hydroxyethyl methacrylate (1/1 mol mixture) and hexamethylene diisocyanate |
| Teslac 2326 | Hitachi Kasei Polymer Co., Inc. | Urethane acrylate oligomer from phenyl glycidyl ether acrylate/2-hydroxypropyl acrylate (1/1 mol mixture) and hexamethylene diisocyanate |
| Teslac 2327 | Hitachi Kasei Polymer Co., Inc. | Urethane acrylate oligomer from phenyl glycidyl ether acrylate/2-hydroxyethyl acrylate (1/1 mol mixture) and hexamethylene diisocyanate |
| NK Oligo UA-4HA | Shin-Nakamura Chemical Co., Ltd | Urethane acrylate oligomer from 3-methacryloyloxy-2-hydroxypropyl acrylate and hexamethylene diisocyanate |

Urethane (Meth)Acrylate Oligomer (B)

TABLE 2

| Trade name | Manufacturer | Composition |
| --- | --- | --- |
| NK Oligo UA-5201 | Shin-Nakamura Chemical Co., Ltd | Polyether polyol type non-yellowing urethane acrylate (molecular weight: about 1,000) |
| NK Oligo UA-160TM | Shin-Nakamura Chemical Co., Ltd | Polytetramethylene glycol type non-yellowing urethane acrylate (molecular weight: about 1,600) |

(2) Other (Meth)Acrylates

TABLE 3

| Trade name | Manufacturer | Composition |
| --- | --- | --- |
| Epoxyester 3000A | Kyoeisha Chemical Co., Ltd | Bisphenol A diglycidyl ether acrylic acid adduct |
| Light ester 3EG | Kyoeisha Chemical Co., Ltd | Triethylene glycol dimethacrylate |
| Epoxyester 3002M | Kyoeisha Chemical Co., Ltd | Epolite 3002 methacylic acid adduct |
| ACMO | | Acryloyloxy morphorine |

(3) Photopolymerization Initiator

TABLE 4

| Trade name | Manufacturer | Composition |
| --- | --- | --- |
| Irgacure 819 | Ciba Specialty Chemicals K.K. Japan | Bis(2,4,6-trimethylbenzoyl) phenylphosphine oxide |
| Irgacure 784 | Ciba Specialty Chemicals K.K. Japan | Bis(cyclopentadienyl)-bis(2,6-difluoro-3-(pyrrol-1-yl)phenyl)titanium |
| Camphorquinone | Sigma-Aldrich Japan K.K. | Camphorquinone |
| Benzophenone | Matsugaki Chemical Industries Co., Ltd | Benzophenone |

(4) Others

TABLE 5

| Trade name | Manufacturer | Composition |
| --- | --- | --- |
| Ethyl dimethylamino-benzoate | Wako Pure Chemical Industries, Ltd. | Ethyl dimethylaminobenzoate |

(5) Light Source:

Fluorescent lamp: 27 W, U-line flat T FML27EX-D (three-band daylight) manufactured by Toshiba Corporation Halogen lamp: Studio & Location Light Tropical TL-500 manufactured by LPL Co., Ltd (halogen lamp 500 W)

Process for Producing a Photocurable Resin:

The photopolymerizable monomer in the amount as indicated in Table A (pg. 49), Table B (pg. 50) or Table E (pg. 52) was put in a flask equipped with a stirrer and a thermometer, and under shading, heating was carried out with stirring and the temperature was raised to 60° C. Then, the polymerization initiator in the amount as indicated in Table A, B or E was added, and stirring and mixing were carried out until the polymerization initiator was dissolved at 60° C.

Preparation of a Photocurable Fixture:

In all of Examples and Comparative Examples, a photocurable resin was applied to a base material at a rate of 300±30 g/m² by a roll coater system.

The one having the photocurable resin applied was cut in a predetermined length, and the predetermined number of pieces as indicated in the figure were overlaid one another, and this was put on a buffering material, further a cover material was put thereon and sewed, and it was enclosed in a non-light-transmissive bag to prepare a splint material.

Further, a predetermined length of a base material having the photocurable resin applied was wound around a core material to form a roll-like shape, and it was enclosed in a non-light-transmissive bag to prepare a casting bandage.

As the base material, a tape-shaped base material obtained by Raschel knitting of glass fibers, with a warp of 14 lines/2.54 cm (1 inch), a weft of 11 lines/2.54 cm, a weight (METSUKE) of 270 g/m², a thickness of 1.02 mm and a width of 100 mm, was used.

Further, a tape-shaped base material (PEs1) obtained by Raschel knitting of polyester fibers, with a warp of 12 lines/2.54 cm, a weft of 9 lines/2.54 cm, a weight (METSUKE) of 200 g/m², a thickness of 0.8 mm and a width of 100 mm, was used.

Moreover, a tape-shaped base material (PEs2) obtained by Raschel knitting of polyester fibers, with a warp of 14 lines/2.54 cm, a weft of 11 lines/2.54 cm, a weight (METSUKE) of 167 g/m², a thickness of 0.8 mm and a width of 100 mm, was also used.

As the buffering material, a needle punched nonwoven fabric of polyester, with a thickness of 2.5 mm and a weight (METSUKE) of 250 g/m$^2$, was used.

As the cover material, a mesh sheet of EVA elastomer with a thickness of 1.5 mm and an open area ratio of 40% was used.

Examples 1 to 9 and Comparative Examples 1 to 5

Photocurable resins were prepared with the proportion of the photopolymerizable monomer, polymerization initiator, etc. as indicated in Table A and Table B, by the above-mentioned process for producing a photocurable resin. Then, using the base materials as indicated in these figures, splint materials were prepared by the above-mentioned process for producing a resin for a photocurable fixture.

Examples 10 to 13

As indicated in Table C (pg. 51), using the photocurable resins of Examples 1, 2, 4 and 5, and using the base cloth of the above PEs1, splint materials with the number of layers of 6 were prepared.

Examples 14 to 17

As indicated in Table D (pg. 51), using the photocurable resin of Example 1 and using the base cloth made of glass fibers, splint materials with the number of layers of 4, 5, 6 or 7 were prepared.

Examples 18 to 23

Photocurable resins were prepared with the proportion of the photopolymerizable monomer, polymerization initiator, etc. in the proportion as indicated in Table E, by the above-mentioned process for producing a photocurable resin. Then, using the base material as indicated in this figure, splint materials were prepared by a process for producing a resin for a photocurable fixture.

Examples 24 to 26 and Comparative Examples 6 to 7

Using the photocurable resins of Examples 1 and 8 and Comparative Examples 1 and 2 as indicated in Table F (pg. 53), and using the base cloth as indicated in this figure, cast materials were prepared.

[[Tests]]

The following tests were conducted for evaluation on the photocurable fixtures and the physical properties of the photocurable resins in the above examples and comparative examples.

As the light source for curing, the above-mentioned fluorescent lamp of 27 W or halogen lamp of 500 W was used.

[Odor]

The odor after the photocurable resin was applied on the base material was evaluated by sensory test.

[Working Time]

In a measuring room adjusted to a room temperature 23° C. and a humidity 65% RH, a photocurable fixture was taken out from a non-light-transmissive bag, and placed 1.5 m below lighted two fluorescent lamps of 40 W which were more intense than the above light source for curing. And, the degrees of curing after 10 minutes and 20 minutes passed were observed to determine whether or not formation could be made.

[Bending Strength]

In a measuring room adjusted to a room temperature 23° C. and a humidity 65% RH, a splint material as a photocurable fixture was taken out from a non-light-transmissive bag, and cut in a length of about 10 cm, and irradiated with the above-mentioned fluorescent lamp of 27 W with the distance and time as indicated in FIGS. 2 to 6. The bending strength after 10 minutes passed from initiation of the irradiation with light was measured.

In the measurement, bending test was carried out in accordance with JIS K7171 with Autograph AG-D (computer measured and controlled precision universal tester, manufactured by Shimadzu Corporation) using a 3-point bending test jig. The 3-point bending test jig had the distance of 50 mm between supporting points and was provided with a supporting portion 11 with the length of 120 mm as shown in FIG. 8. A specimen 13 was put on this supporting portion 11, and a load was applied with an indentor 12 having a length of 110 mm. The testing speed was 100 mm/min.

[Cylinder Strength]

In a measuring room adjusted to a room temperature 23° C. and a humidity 65% RH, a roll-shaped cast material as a photocurable fixture was taken out from a non-light-transmissive bag, and wound around a stainless tube having a diameter of 60.5 mm maintained substantially horizontally, in five layers, to prepare a cylinder. And, after the winding, the cylinder was suppressed by both hands and its surface was rubbed. Using the above fluorescent lamp of 27 W, the cylinder was irradiated with light for 30-second with the distance of 2 cm from four directions of upper, lower, left and right, so that the cylinder would be cured uniformly. After 5 minutes passed from completion of the irradiation, the cast material was pulled out from the stainless tube taking care so that no deformation would occur, and used as a specimen 16. After 10 minutes and 24 hours passed from initiation of the irradiation with light, stress of the cylinder was measured with the Autograph using a 3-point bending test jig. The 3-point bending test jig had the distance of 50 mm between supporting points and was provided with a supporting portion 14 having a length of 120 mm, as shown in FIG. 9. On the supporting portion 14, the cylinder-shaped specimen 16 was placed so that its longitudinal direction would be parallel with the longitudinal direction of the supporting portion 14. And, under such conditions that the testing speed was 100 mm/min, the cylinder was compressed with a disc indentor 15 having a diameter of 100 mm from the upper side, and the stress when 5 mm deformation was observed was measured.

[Heat Generation Temperature]

In a measuring room adjusted to a room temperature 23° C. and a humidity 65% RH, a photocurable fixture was taken out from a non-light-transmissive bag. A square polyethylene vessel warmed at 37° C. in advance by placing warm water therein, was provided with a temperature sensor on its surface, and the above photocurable fixture was put thereon. Using the above fluorescent lamp of 27 W, irradiation was carried out with the light source, and distance and time as indicated in Tables A-F to cure the photocurable fixture and the maximum heat generation temperature were measured.

[Gurley Permeability]

A disc-shaped specimen having a diameter of 40 mm was cut out of the cured photocurable fixture, and the permeability of air of 350 ml was measured with a Gurley permeability tester.

[[Results of Tests]]

The measurement results concerning the physical properties and evaluations of respective Examples and Comparative Examples are indicated in Tables A-F, etc.

[Odor]

With the photocurable resins in Comparative Examples 1 to 3, acid smell was recognized, and this was particularly strong in Comparative Example 2.

In Examples and other Comparative Examples, such odor was not recognized, and these were well in this point.

[Working Time]

In respective Examples, the working period was at least 20 minutes. Namely, in this working period test, a bending strength was measured with respect to the ones that had been irradiated with light for 20 minutes. The ones already irradiated with light in this manner similarly cured like the ones immediately used, and showed the strength of at least 500 N as the splint and at least 300 N as the cast.

If the working period of such length can be obtained, it is possible to securely apply the fixture with ample time even to a complicated site of affected parts. In a water-curable fixture for orthopedic surgery, the working period is usually 1 minute 50 seconds to 2 minutes 30 seconds after the fixture is immersed in water.

[Bending Strength]

In the conventionally used water-curable splint material, if the strength (initial strength) at the point of about 10 minutes later does not reach at least about 150 N, such material is not practically used. Further, as the strength after 24 hours, it is considered that at least 500 N is necessary for fixing the affected parts.

In the case of a photocurable splint material, the curing is almost completed during the irradiation with light, and thereafter, increase in strength can hardly be seen as the lapse of time. In respective Examples in Tables A-E, since at least 500 N can be obtained after 10 minutes, these fixtures satisfy the required strength after 24 hours of the water-curable splint material, and thus it is found that sufficient curing properties are possessed.

On the contrary, in Comparative Examples in Table B, the strength is less than 150 N, and substantially no change is seen after 24 hours, namely, these are all less than 500 N and insufficient in strength. Further, as mentioned above, odor is recognized in Comparative Examples 1 to 3 and these cannot be suitably applied to the use of the present invention in this point as well.

[Cylinder Strength]

As the conventionally used water-curable cast material, if the cylinder strength does not reach at least about 80 N at the point of about 10 minutes later, such material cannot be practically used. Further, as the strength after 24 hours, it is considered that at least 300 N is required to fix the affected parts.

In the case of a photocurable cast material, similarly to the splint material, the curing is almost completed during the irradiation with light, and thereafter, increase in strength can hardly be seen as the lapse of time. In respective Examples in Table F, since at least 400 N can be obtained after 10 minutes, these fixtures satisfy the required strength after 24 hours of the water-curable cast material, and thus it is found that sufficient curing properties are possessed.

On the contrary, in Comparative Examples 6 and 7, the strength is at least 80 N in 10 minutes, and substantially no change is seen after 24 hours, namely, these are all less than 300 N and insufficient in strength.

[Heat Generation Temperature]

If the temperature is overly raised by heat generation during the curing time, burning will be caused. In usual, if the maximum temperature is 40° C. or lower, no burning will be caused. In all of the Examples, the maximum temperature is 40° C. or lower, and it is found that no problem is recognized in the heat generation temperature as well.

[Gurley Permeability]

The Gurley permeability required so as not to cause stuffiness at the affected parts, is 1 second or lower. In Examples 14 to 17 in Table D, the measured Gurley permeability is within a range of 0.2 to 0.6 second, and shows that sufficient air permeability can be secured.

[Total Evaluation]

As mentioned above, with the photocurable resins in the Examples, no substantial odor is recognized and sufficient working period as a fixture can be obtained. Further, the heat generation temperature is 40° C. or lower in all cases at the time of using the photocurable fixture, and no inconvenience is seen in use. In the bending strength of the splint material and the cylinder strength of the cast material, sufficient strength can be obtained in both initial curing properties and final curing properties (after 24 hours), and these can be suitably used as the fixture.

On the other hand, with the ones in the Comparative Examples, both bending strength and cylinder strength are low, and it is impossible to obtain sufficient initial curing properties. Further, some of the photocurable resins have odor and cannot be suitably used.

TABLE A

|  | Ex. 1 | Ex. 2 | Ex. 3 | Ex. 4 | Ex. 5 | Ex. 6 | Ex. 7 |
|---|---|---|---|---|---|---|---|
| AH-600 | 995 | | | | | | |
| Teslac 2324 | | 995 | | | | | |
| Teslac 2325 | | | 995 | | | | |
| Teslac 2326 | | | | 995 | | | |
| Teslac 2327 | | | | | 995 | | |
| UA-306H | | | | | | 995 | |
| NK Oligo UA-4HA | | | | | | | 995 |
| Irgacure 819 | 5 | 5 | 5 | 5 | 5 | 5 | 5 |
| Odor | *1 | *1 | *1 | *1 | *1 | *1 | *1 |
| Base material | PEs1 | PEs1 | PEs1 | PEs1 | PEs1 | Glass | Glass |
| Number of layers | 6 | 6 | 6 | 6 | 6 | 6 | 6 |
| Working period | *2 | *2 | *2 | *2 | *2 | *2 | *2 |
| Light source | *3 | *3 | *3 | *3 | *3 | *3 | *3 |
| Irradiation distance (cm) | 2 | 2 | 2 | 2 | 2 | 2 | 2 |
| Irradiation time (sec.) | 80 | 80 | 80 | 80 | 80 | 80 | 80 |
| Bending strength (N) | 652 | 635 | 825 | 767 | 832 | 546 | 890 |

*1: substantially no odor, *2: at least 20 minutes, *3: 27 W fluorescent lamp

TABLE B

|  | Ex. 8 | Ex. 9 | Comp. Ex. 1 | Comp. Ex. 2 | Comp. Ex. 3 | Comp. Ex. 4 | Comp. Ex. 5 |
|---|---|---|---|---|---|---|---|
| AH-600 | 940 | 940 | | | | | |
| Epoxy ester 3000A | | | 995 | | | | |
| Light ester 3EG | | | | 995 | | | |
| Epoxy ester 3002M | | | | | 995 | | |
| ACMO | 50 | 50 | | | | | |
| NK Oligo UA-5201 | | | | | | 995 | |
| NK Oligo UA-160TM | | | | | | | 995 |
| Irgacure 819 | 5 | 10 | 5 | 5 | 5 | 5 | 5 |
| Odor | *1 | *1 | *4 | *5 | *4 | *1 | *1 |
| Base material | PEs1 | PEs2 | Glass | Glass | Glass | Glass | Glass |
| Number of layers | 6 | 6 | 6 | 6 | 6 | 6 | 6 |

TABLE B-continued

|  | Ex. 8 | Ex. 9 | Comp. Ex. 1 | Comp. Ex. 2 | Comp. Ex. 3 | Comp. Ex. 4 | Comp. Ex. 5 |
|---|---|---|---|---|---|---|---|
| Working period | *2 | *2 | *2 | *2 | *2 | *2 | *2 |
| Light source | *3 | *3 | *3 | *3 | *3 | *3 | *3 |
| Irradiation distance (cm) | 2 | 2 | 2 | 2 | 2 | 2 | 2 |
| Irradiation time (sec.) | 80 | 80 | 80 | 80 | 80 | 80 | 80 |
| Bending strength (N) | 638 | 688 | 78 | 103 | 89 | 125 | 70 |

*1: substantially no odor, *2: at least 20 minutes, *3: 27 W fluorescent lamp, *4: acid smell, *5: strong acid smell

TABLE C

|  | Ex. 10 | Ex. 11 | Ex. 12 | Ex. 13 |
|---|---|---|---|---|
| Resin | Resin of Ex. 1 | Resin of Ex. 2 | Resin of Ex. 4 | Resin of Ex. 5 |
| Base material | PEs1 | PEs1 | PEs1 | PEs1 |
| Number of layers | 6 | 6 | 6 | 6 |
| Light source | *3 | *3 | *3 | *3 |
| Irradiation distance (cm) | 5 | 5 | 5 | 5 |
| Irradiation time (min.) | 2 | 2 | 2 | 2 |
| Bending strength (N) | 646 | 649 | 561 | 561 |

*3: 27 W fluorescent lamp

TABLE D

|  | Ex. 14 | Ex. 15 | Ex. 16 | Ex. 17 |
|---|---|---|---|---|
| Resin | Resin of Ex. 1 | Resin of Ex. 1 | Resin of Ex. 1 | Resin of Ex. 1 |
| Base material | Glass | Glass | Glass | Glass |
| Number of layers | 4 | 5 | 6 | 7 |
| Light source | *3 | *3 | *3 | *3 |
| Irradiation distance (cm) | 2 | 2 | 2 | 2 |
| Irradiation time (sec.) | 80 | 80 | 80 | 80 |
| Bending strength (N) | 560 | 823 | 1056 | 1317 |
| Gurley permeability | 0.2 | 0.3 | 0.4 | 0.6 |

*3: 27 W fluorescent lamp

TABLE E

|  | Ex. 18 | Ex. 19 | Ex. 20 | Ex. 21 | Ex. 22 | Ex. 23 |
|---|---|---|---|---|---|---|
| AH-600 | 995 | 999 | 999 | 999.5 | 990 | 995 |
| Irgacure 819 | 5 |  |  |  |  | 5 |
| Irgacure 784 |  | 1 | 1 | 0.5 |  |  |
| Camphorquinone |  |  |  |  | 5 |  |
| Ethyl dimethylamino benzoate |  |  |  |  | 5 |  |
| Benzophenone |  |  |  |  |  |  |
| Odor | *1 | *1 | *1 | *1 | *1 | *1 |
| Base material | PEs1 | PEs1 | Glass | PEs1 | PEs1 | Glass |
| Number of layers | 6 | 6 | 6 | 6 | 6 | 6 |
| Working period | *2 | *2 | *2 | *2 | *2 | *2 |
| Light source | *3 | *3 | *3 | *3 | *3 | *6 |
| Irradiation distance (cm) | 10 | 10 | 10 | 10 | 10 | 20 |
| Irradiation time (sec.) | 80 | 80 | 80 | 80 | 80 | 40 |
| Bending strength (N) | 698 | 834 | 1213 | 734 | 728 | 803 |

*1: substantially no odor, *2: at least 20 minutes, *3: 27 W fluorescent lamp, *6: 500 W halogen lamp

TABLE F

|  | Ex. 24 | Ex. 25 | Ex. 26 | Comp. Ex. 6 | Comp. Ex. 7 |
|---|---|---|---|---|---|
| Resin | Resin of Ex. 1 | Resin of Ex. 1 | Resin of Ex. 8 | Resin of Comp. Ex. 1 | Resin of Comp. Ex. 2 |
| Base material | PEs1 | Glass | PEs1 | Glass | Glass |
| Number of layers by winding | 5 | 5 | 5 | 5 | 5 |
| Light source | *3 | *3 | *3 | *3 | *3 |
| Irradiation distance (cm) | 2 | 2 | 2 | 2 | 2 |
| Irradiation time (sec.) in one direction [×4 directions] | 30 | 30 | 30 | 30 | 30 |
| Cylinder strength (10 min. after) | 461 | 699 | 407 | 77 | 57 |
| Cylinder strength (24 hr after) | 470 | 725 | 421 | 83 | 61 |

*3: 27 W fluorescent lamp

The invention claimed is:

1. A photocurable orthopedic fixture for orthopedic surgery, the photocurable orthopedic fixture comprising:
a base material; and
a photocurable resin retained in the base material and containing a urethane (meth)acrylate oligomer and a photopolymerization initiator which absorbs a light within a range of 400 to 700 nm, the urethane (meth)acrylate oligomer being represented by the following formula (I),

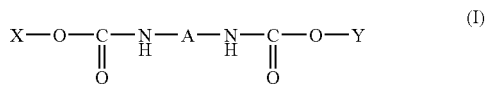

where A denotes a diisocyanate residue selected from an aliphatic or an alicyclic diisocyanate, and each of X and Y denotes a residue obtained by removing a hydroxy group from a (meth)acrylate having a hydroxy group;
wherein in formula (I) at least 40 mol % of X and Y is a residue obtained by removing a hydroxy group from a (meth)acrylate having a hydroxy group represented by the following formula (II),

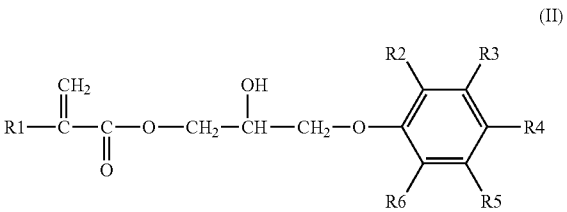

where in Formula (II) each of R1 to R6 denotes a hydrogen atom or a methyl group.

2. A photocurable orthopedic fixture for orthopedic surgery according to claim 1; wherein the photopolymerization initiator is a bisacylphosphine oxide type photopolymerization initiator represented by the following formula (III),

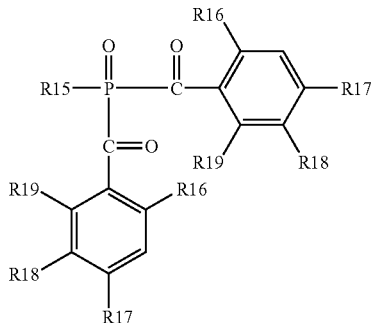
(III)

where R15 denotes a straight chain or branched chain $C_{1-12}$ alkyl group, a cycloalkyl group, an aryl group which may be substituted by a straight chain or branched chain $C_{1-12}$ alkyl group or a halogen atom; each of R16 and R17 which may be the same or different, denotes a hydrogen atom, a straight chain or branched chain $C_{1-12}$ alkyl group, or a straight chain or branched chain $C_{1-12}$ alkoxy group; and where each of R18 and R19 which may be the same or different, denotes a hydrogen atom, or a straight chain or branched chain $C_{1-12}$ alkyl group.

3. A photocurable orthopedic fixture for orthopedic surgery according to claim 2; wherein the photopolymerization initiator represented by formula (III) is bis(2,4,6-trimethylbenzoyl)phenyl phosphine oxide.

4. A photocurable orthopedic fixture for orthopedic surgery, the photocurable orthopedic fixture comprising:
a base material; and
a photocurable resin retained in the base material and containing a urethane (meth)acrylate oligomer and a photopolymerization initiator which absorbs a light within a range of 400 to 700 nm, the urethane (meth)acrylate oligomer being represented by the following formula (I),

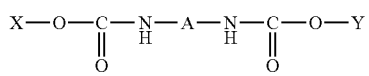
(I)

where A denotes a diisocyanate residue selected from a diisocyanate other than an aromatic diisocyanate, and each of X and Y denotes a residue obtained by removing a hydroxy group from a (meth)acrylate having a hydroxy group;
wherein in formula (I) at least 40 mol % of X and Y is a residue obtained by removing a hydroxy group from a (meth)acrylate having a hydroxy group represented by the following formula (II),

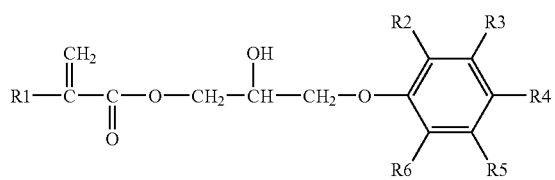
(II)

where in Formula (II) each of R1 to R6 denotes a hydrogen atom or a methyl group.

5. A photocurable orthopedic fixture for orthopedic surgery according to claim 4; wherein the photopolymerization initiator is a bisacylphosphine oxide type photopolymerization initiator represented by the following formula (III),

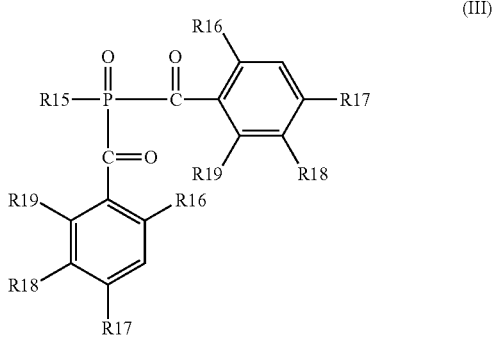
(III)

where R15 denotes a straight chain or branched chain $C_{1-12}$ alkyl group, a cycloalkyl group, an aryl group which may be substituted by a straight chain or branched chain $C_{1-12}$ alkyl group or a halogen atom; each of R16 and R17 which may be the same or different, denotes a hydrogen atom, a straight chain or branched chain $C_{1-12}$ alkyl group, or a straight chain or branched chain $C_{1-12}$ alkoxy group; and where each of R18 and R19 which may be the same or different, denotes a hydrogen atom, or a straight chain or branched chain $C_{1-12}$ alkyl group.

6. A photocurable orthopedic fixture for orthopedic surgery according to claim 5; wherein the photopolymerization initiator represented by formula (III) is bis(2,4,6-trimethylbenzoyl)phenyl phosphine oxide.

7. A photocurable orthopedic fixture for orthopedic surgery, the photocurable orthopedic fixture comprising:
a base material; and
a photocurable resin retained in the base material and containing a urethane (meth)acrylate oligomer and a photopolymerization initiator which absorbs a light within a range of 400 to 700 nm, the urethane (meth)acrylate oligomer being represented by the following formula (I),

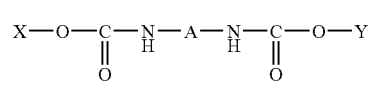
(I)

where A denotes a diisocyanate residue selected from an aliphatic or an alicyclic diisocyanate, and each of X and Y denotes a residue obtained by removing a hydroxy group from a (meth)acrylate having a hydroxy group;
wherein in formula (I) at least 40 mol % of X and Y is a residue obtained by removing a hydroxy group from a (meth)acrylate having a hydroxy group represented by the following formula (II),

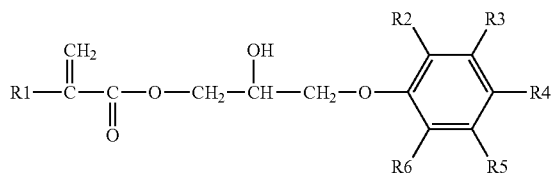
(II)

where each of R1 to R6 denotes a hydrogen atom or a methyl group; and
wherein the photopolymerization initiator is a titanocene type photopolymerization initiator represented by the following formula (IV),

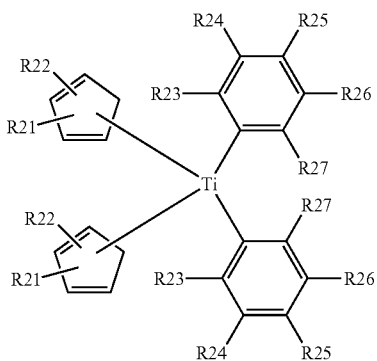 (IV)

where each of R21 and R22 independently denotes a hydrogen atom or a methyl group; R23 denotes a fluorine atom, —$CF_3$ or —$CF_2CH_3$; and each of R24, R25, R26 and R27 independently denotes a hydrogen atom, a fluorine atom, —$CF_3$, —$CF_2CH_3$, a $C_1$-$C_{12}$ alkyl group or alkoxy group, a 6-membered carbocyclic aromatic group, or a 5- or 6-membered heterocyclic aromatic group.

8. A photocurable orthopedic fixture for orthopedic surgery according to claim 7; wherein the photopolymerization initiator represented by formula (IV) is bis(cyclopentadienyl)-bis(2,6-difluoro-3-(pyrrol-1-yl)phenyl)titanium.

* * * * *